United States Patent [19]

Wakabayashi et al.

[11] Patent Number: 5,034,414

[45] Date of Patent: Jul. 23, 1991

[54] LIQUID EMULSION FOR TRANSFUSION

[75] Inventors: Toshio Wakabayashi; Kazuo Okamoto, both of Tokyo; Akio Kanazawa, Kagoshima, all of Japan

[73] Assignee: Terumo Kabushiki Kaisha, Tokyo, Japan

[21] Appl. No.: 349,892

[22] Filed: May 5, 1989

Related U.S. Application Data

[63] Continuation of Ser. No. 136,511, Dec. 22, 1987, abandoned, which is a continuation of Ser. No. 898,758, Aug. 13, 1983, abandoned, which is a continuation of Ser. No. 587,175, Mar. 7, 1984, abandoned.

[30] Foreign Application Priority Data

Mar. 18, 1983 [JP] Japan ..................... 58-45618

[51] Int. Cl.$^5$ .................... A61K 31/22; A61K 31/23
[52] U.S. Cl. .................... 514/549; 514/552; 514/560; 424/523
[58] Field of Search ............ 514/552, 549, 560; 424/523

[56] References Cited

U.S. PATENT DOCUMENTS

| | | | |
|---|---|---|---|
| 2,819,199 | 1/1958 | Kalish | 424/312 |
| 2,853,419 | 9/1958 | Degkwitz | 424/312 |
| 2,972,565 | 2/1961 | Zilversmit | 424/312 |
| 3,676,472 | 7/1972 | Zilliken et al. | 424/312 |
| 3,873,720 | 3/1975 | Suzuki et al. | 424/312 |

FOREIGN PATENT DOCUMENTS

| | | | |
|---|---|---|---|
| 0071995 | 2/1983 | European Pat. Off. | |
| 3213744 | 11/1982 | Fed. Rep. of Germany | |
| 3131460 | 2/1983 | Fed. Rep. of Germany | |
| 3403251 | 8/1984 | Fed. Rep. of Germany | |
| 964156 | 11/1965 | France | 424/312 |
| 0122312 | 9/1981 | Japan | 424/312 |
| 785387 | 10/1957 | United Kingdom | |
| 1413451 | 11/1975 | United Kingdom | |
| 2033745 | 5/1980 | United Kingdom | |
| 2098065 | 11/1982 | United Kingdom | 424/312 |

OTHER PUBLICATIONS

Hagers Handbuch der pharm. Praxis, 4. Ausg., 7.Bd., Teil A, Springer Verlag Berlin, 1971, S. 405–407.

*Primary Examiner*—Sam Rosen
*Attorney, Agent, or Firm*—Frishauf, Holtz, Goodman & Woodward

[57] ABSTRACT

A nutritional liquid emulsion for transfusion comprising of a mixture of fatty acid esters containing 20–22 carbon atoms which are contained in a purified fish oil selected from the group consisting of sardine oil, cod oil, squid oil, mackerel oil or Euphauciacea oil, of a purified soybean or safflower oil, of purified yolk lecithin or soybean lecithin and the balance water. Said nutritional liquid emulsion for transfusion is well balanced in fatty acid composition and is nutritionally valuable and also possesses antithorombotic activity and antiarteriosclerotic activity.

9 Claims, No Drawings

LIQUID EMULSION FOR TRANSFUSION

This application is a continuation of application Ser. No. 07/136,511, filed Dec. 22, 1987 which is a continuation of Ser. No. 06/898,758 filed Aug. 13, 1986 (abandoned); which is a continuation of Ser. No. 06/587,175 filed Mar. 7, 1984 (abandoned).

BACKGROUND OF THE INVENTION

1. Field of the Invention

The present invention relates to an improved liquid emulsion for transfusion.

More particularly, it is concerned with a liquid emulsion for transfusion well balanced in fat composition.

The liquid emulsion for transfusion is administered to patients for nutritional supplement. It is intravenously introduced usually by drop infusion.

2. Description of the Prior Art

The liquid emulsion for transfusion is an emulsion composed of fat, an emulsifier and water. Prior-art liquid emulsions for transfusion employ vegetable oil such as purified soybean oil. Whereas vegetable oils are rich in fatty acids containing 18 or less carbon atoms such as oleic acid, palmitic acid, linoleic acid, linolenic acid and stearic acid, they contain none of fatty acids containing 20 or more carbon atoms. In human blood and cells, however, there are also contained fatty acids containing 20 or more carbon atoms such as eicosapentaenoic acid and docosahexaenoic acid in considerable amounts so that prior-art liquid emulsions for transfusion containing as the fat component vegetable oil only are not nutritionally balanced and unsatisfactory.

SUMMARY OF THE INVENTION

It is an object of this invention to provide an improved liquid emulsion (fat emulsion) for transfusion well balanced nutritionally.

Another object of the invention is to provide a liquid emulsion for transfusion possessing an antithrombotic activity.

As a result of extensive studies we have been successful in preparing a liquid emulsion for transfusion containing one or more of fatty acids of 20-22 carbon atoms or esters thereof such as eicosapentaenoic acid and docosahexaenoic acid or esters thereof and found that said liquid emulsion for transfusion has an antithrombotic activity.

According to the present invention, there is provided a liquid emulsion for transfusion comprising a fatty acid containing 20-22 carbon atoms or an ester thereof or a mixture of two or more of the fatty acids and the esters, a vegetable oil, an emulsifier and water.

Further according to the invention, there is provided a liquid emulsion for transfusion wherein the above-mentioned fatty acid or ester is an unsaturated fatty acid or an ester thereof.

Further according to the invention, there is provided a liquid emulsion for transfusion wherein the above-mentioned fatty acid or the ester is eicosapentaenoic acid, docosahexaenoic acid or an ester thereof.

Further according to the invention, there is provided a liquid emulsion for transfusion wherein the above-mentioned mixture of fatty acids or esters thereof is a purified fish oil.

Further according to the invention, there is provided a liquid emulsion for transfusion wherein the above-mentioned purified fish oil is purified sardine oil.

Further according to the invention, there is provided a liquid emulsion for transfusion wherein the above-mentioned vegetable oil is purified soybean oil and/or safflower oil.

Further according to the invention, there is provided a liquid emulsion for transfusion comprising 5-20 w/v % of the above-mentioned fatty acid or the ester or the mixture thereof, 1-19 w/v % of a vegetable oil, 1-2 w/v % of an emulsifier and water (the balance).

DETAILED DESCRIPTION OF THE INVENTION

The present invention is directed to a liquid emulsion for transfusion comprising a fatty acid containing 20-22 carbon atoms or an ester thereof or a mixture of two or more of the fatty acids and the esters, a vegetable oil, an emulsifier and water.

The liquid emulsion for transfusion according to the invention is characterized by containing a fatty acid having 20-22 carbon atoms or an ester of the fatty acid or a mixture of two or more of the fatty acids and the esters. As the preferred fatty acids used in the invention are mentioned fatty acids containing 20-22 carbon atoms such as eicosapentaenoic acid and docosahexaenoic acid. Preferred esters of these fatty acids are the triglycerides or the lower alkyl esters (for example, the ethyl ester). The esters contain 20-22 carbon atoms in the fatty acid moiety. As the glyceride of the fatty acids may be employed those separated and purified from fish oil. The lower alkyl esters are prepared by reacting the fatty acid with a lower alcohol in a conventional manner or by an ester exchange by reacting triglyceride of the fatty acid with a lower alcohol.

In the present invention, a mixture of two or more of the above-mentioned fatty acids or esters thereof may also be used. As the mixture may be employed fish oil such as, sardine oil, cod oil, squid oil, mackerel oil or Euphauciacea oil which is preferably purified to reduce adverse reactions to the living body. Purified sardine oil, which is rich in eicosapentaenoicacid, docosahexaenoic acid and esters of these acids is particularly preferred as the fat component in the present invention. Unexpectedly from the prior art and surprisingly, we have found that fish oil such as sardine oil can safely employed as a component of the formulation for intravenous administration.

The vegetable oil and the emulsifier to be employed in the invention may be any of the conventional ones.

For example, purified soybean oil, safflower oil or the like or a mixture thereof is used as the vegetable oil, and purified yolk lecithin, purified soybean lecithin or the like is used as the emulsifier.

Besides, there may be added to the liquid emulsion for transfusion of the invention an appropriate amount of an emulsion stabilizer or emulsion promoter such as glycerin or oleic acid.

Although components of the liquid emulsion for transfusion according to the invention may be used in any proportions, it is preferable to use 5-20 w/v % of a fatty acid containing 20-22 carbon atoms or an ester of the fatty acid or a mixture of two or more of the fatty acids and the esters, 1-19 w/v % of a vegetable oil, 1-2 w/v % of an emulsifier and water (the balance). The emulsion stabilizer or emulsion promoter is employed usually the range of 1-5 w/v %.

To emulsion of the invention may be added vitamin E in order to prevent oxidation of the unsaturated fatty acids. Fat particles in the emulsion are not broken and kept very stable by the addition.

The liquid emulsion for transfusion is prepared according to a conventional process. Predetermined amounts of the components are blended. To the blend is added an alkali to promote dispersion, and a uniform dispersion is made by means of a homomixer. To the dispersion is added injectable distilled water, and the mixture is subjected to emulsification by means of a high pressure spray emulsifier to prepare the liquid emulsion for transfusion. The emulsion is subdivided into plastic bags which are steam sterilized under high pressure and film packed in vacuum to give the final product.

The liquid emulsion for transfusion, which contains nutritionally required fatty acids in a well balanced proportion, is an excellent nutritional supplement.

As the liquid emulsion for transfusion contains eicosapentaenoic acid and/or docosahexaenoic acid or esters thereof, it possesses a platelet aggregation-inhibitory activity and is also useful as an antithrombotic agent.

Moreover, as the liquid emulsion for transfusion contains triglycerides of fatty acids such as eicosapentaenoic acid and/or docosahexaenoic acid, it reduces blood cholesterol and is useful for prevention or therapy of arteriosclerosis.

The invention will be described in more details below by means of examples and a test example.

EXAMPLE 1

A mixture of 20 g. of ethyl 5,8,11,14,17-eicosapentaenoate, 380 g. of purified soybean oil, 48 g. of purified yolk lecithin, 20 g. of oleic acid, 100 g. of concentrated glycerin and 40 ml. of 0.1N-sodium hydroxide was dispersed by means of a homomixer. To the dispersion was added injectable distilled water to a total volume of 4 l. The resulting mass was emulsified by means of a high pressure spray emulsifier to prepare a liquid emulsion. The liquid emulsion was subdivided into plastic bags in 200-ml. portions, which were steam sterilized under high pressure at 121° C. for 20 min. to prepare a liquid emulsion for transfusion. After the sterilization, the bag was packed in oriented vinylon film (a product of UNITIKA Co., Ltd.) under vacuum to give the final product.

EXAMPLE 2

A liquid emulsion for transfusion was prepared in the same way as in Example 1 except that the 20g. of ethyl eicosapentaenoate and the 380 g. of purified soybean oil used therein were substituted with 40 g. of ethyl 4,7,10,13,16,19-docosahexaenoate and 360 g. of purified soybean oil, respectively.

EXAMPLE 3

A mixture of 120 g. of highly purified sardine oil containing 18% of 5,8,11,14,17-eicosapentaenoic acid and 10% of 4,7,10,13,16,19-docosahexaenoic acid and of a fat composition shown in Table 1 (which is an example of fat composition in purified sardine oil), 280 g. of purified soybean oil, 48 g. of purified yolk lecithin, 2.0 g. of oleic acid, 100 g. of concentrated glycerin and 40 ml. of 0.1N-sodium hydroxide was dispersed by means of a homomixer. To the dispersion was added injectable distilled water to a total volume of 4 l. The resulting mass was emulsified by means of a high pressure spray emulsifier to prepare a liquid emulsion containing 30 w/v % of the fish oil. The emulsion was subdivided into plastic bags in 200-ml. portions, which were steam sterilized under high pressure at 121° C. for 20 min. to prepare a liquid emulsion for transfusion. After the sterilization, the bag was packed in oriented vinylon film (a product of UNITIKA Co., Ltd.) under vacuum to prepare the final product.

TABLE 1

| Fat composition in a purified sardine oil. | |
|---|---|
| Fat | Content (%) |
| Hydrocarbon | 3.61 |
| Steryl ester | 6.84 |
| Triglyceride | 46.50 |
| Free fatty acid | 36.52 |
| Sterol | 6.53 |

TEST EXAMPLE

Platelet aggregation-inhibitory activity

Sixteen male Wister rats weighing about 310 g. were catetherized through the jugular vein. Four of the animals were daily infused over 3 hours with 12 ml. of a commercially available liquid emulsion containing 10 w/v % of soybean oil (control) through the jugular vein for 7 days. In addition, the animals were orally administered with 14 g. of a solid powder feed (CE-2; manufactured by Nihon Clea Co., Ltd.) per day for 7 days. The remainder 12 animals divided into 3 groups, and each group of animals were infused with 12 ml. of the liquid emulsion obtained in Examples 1, 2 and 3, respectively, in the same way as above, daily over 3 hours over 7 days. The animals were also administered with the solid powder feed in the same way as above, 14 g. per day for 7 days. About 20 hours after the final jugular intravenous administration, each animal was anesthesized with 5% Nembutol, from which 4.5 ml. of blood was drawn through the abdominal aorta with a 20 G needle into a syringe containing 0.5 ml. of 3.8% sodium citrate. A PRP of 500,000 platelets/ $\mu$l. was prepared for each rat in a conventional manner. In a curette was placed 225 $\mu$l. of the PRP from each rat. To the curette after warming at 37° C. for 5 min. was added 25 $\mu$l. of collagen (750 $\mu$g./ml.), an aggregation inducer, followed by measurement of the platelet aggregation by means of an aggregometer. As shown in Table 2, the average ratios of aggregation in the groups administered with the liquid emulsions of Examples 1, 2 and 3 were respectively 59.6%, 54.3% and 59.4%. As compared with the control in which it was 68.3%, the platelet aggregation was significantly reduced with a significance level of 5% (t test). Results of acute toxicity tests in rats (male) indicated that the liquid emulsions of Examples 1, 2 and 3 were quite safe.

TABLE 2

| Liquid emulsion for transfusion | No. of the tested rat | Percent platelet aggregation | Average percent aggregation |
|---|---|---|---|
| Example 1 | 1 | 59.0 | |
|  | 2 | 60.7 | 59.6 |
|  | 3 | 56.8 | |
|  | 4 | 61.9 | |
| Example 2 | 5 | 57.5 | |
|  | 6 | 50.7 | 54.3 |
|  | 7 | 52.0 | |
|  | 8 | 56.8 | |
| Example 3 | 9 | 54.7 | |
|  | 10 | 60.6 | 59.4 |
|  | 11 | 61.9 | |
|  | 12 | 60.5 | |
| Control | 13 | 74.6 | |

TABLE 2-continued

| Liquid emulsion for transfusion | No. of the tested rat | Percent platelet aggregation | Average percent aggregation |
|---|---|---|---|
| | 14 | 63.9 | 68.3 |
| | 15 | 70.6 | |
| | 16 | 63.9 | |

Male rats were administered with the liquid emulsions of Example 1, 2 and 3 and the control one respectively through the jugular vein at an infusion rate of 50 ml./kg./hr. to determine the acute toxicity. Results are shown in Table 3. As clearly seen from Table 3, the liquid emulsions for transfusion according to the invention are quite safe preparations.

TABLE 3

| Fat emulsion for transfusion | Lethal dose (ml./kg.) |
|---|---|
| Example 1 | 375 |
| Example 2 | 362 |
| Example 3 | 382 |
| Control | 355 |

What is claimed is:

1. A method of supplying nutrition to a mammal which comprises administering by intravenous transfusion to the said mammal a nutritional emulsion well balanced in fat composition for transfusion comprising 0.8 to 20 w/v % of a mixture of
   (a) 5,8,11,14,17-eicosapentaenoic acid or an ester thereof and
   (b) 4,7,10,13,16,19-docosahexaenoic acid or an ester thereof which mixture is contained in a purified sardine oil, 1-19 w/v % of a purified soybean or safflower oil, 1-2 w/v % of purified yolk lecithin or soybean lecithin, 1-5 w/v % emulsion stabilizer and the balance water.

2. The method of claim 1 wherein the emulsion comprises 0.84-20 w/v % of said mixture of (a) and (b).

3. The method of claim 1 wherein the vegetable oil is purified soybean oil.

4. A method for preparing a nutritional liquid emulsion for transfusion, comprising
   emulsifying in an aqueous carrier, 1-19 w/v % vegetable oil, 1-5 w/v % emulsion stabilizer and 0.8 to 20 w/v % of a mixture of
   (a) 5,8,11,14,17-eicosapentaenoic acid or an ester thereof and
   (b) 4,7,10,13,16,19-docosahexaenoic acid or an ester thereof which are contained in a purified sardine oil.

5. The method of claim 4 wherein 0.84-20 w/v % of said mixture of (a) and (b) are used.

6. The method of claim 4 wherein said aqueous carrier contains 1-19% w/v of a purified soybean or safflower oil, and 1-2% w/v of purified yolk lecithin or soybean lecithin and the balance is water.

7. The method of claim 4 wherein the vegetable oil is purified soybean oil.

8. A nutritional emulsion for transfusion well balanced in fat composition which comprises 0.8 to 20 w/v % of a mixture of (a) 5,8,11,14,17-eicosapentaenoic acid or an ester thereof and (b) 4,7,10,13,16,19-docosahexaenoic acid or an ester thereof which are contained in a purified sardine oil, 1-19 w/v % of a purified soybean or safflower oil, 1-2 w/v % of purified egg yolk lecithin or soybean lecithin, 1-5 w/v % emulsion stabilizer and the balance water.

9. The emulsion of claim 8 wherein the purified soybean oil is used.

* * * * *